United States Patent
Tohyama et al.

(10) Patent No.: US 7,358,063 B2
(45) Date of Patent: Apr. 15, 2008

(54) METHOD OF DETECTING PS2V (75) Inventors: Masaya Tohyama, 9-3, Shinsenrikitamachi 2-chome, Toyonaka-shi, Osaka 560-0081 (JP); Yuichi Yasuda, Kobe (JP); Yasushi Hasui, Kobe (JP); Hideki Ishihara, Kobe (JP); Koichi Yamagata, Kobe (JP)

(73) Assignees: Sysmex Corporation, Hyogo (JP); Masaya Tohyama, Osaka (JP)

( * ) Notice: Subject to any disclaimer, the term of this patent is extended or adjusted under 35 U.S.C. 154(b) by 365 days.

(21) Appl. No.: 10/484,152

(22) PCT Filed: Jul. 17, 2002

(86) PCT No.: PCT/JP02/07281

§ 371 (c)(1),
(2), (4) Date: Mar. 8, 2004

(87) PCT Pub. No.: WO03/008970

PCT Pub. Date: Jan. 30, 2003

(65) Prior Publication Data
US 2005/0003339 A1    Jan. 6, 2005

(30) Foreign Application Priority Data
Jul. 19, 2001    (JP)    ............................. 2001-219860

(51) Int. Cl.
G01N 33/53    (2006.01)
G01N 33/537   (2006.01)
G01N 33/542   (2006.01)
G01N 1/30     (2006.01)
G01N 33/566   (2006.01)
G01N 33/567   (2006.01)
G01N 33/48    (2006.01)

(52) U.S. Cl. .................... 435/7.94; 435/7.9; 435/7.92; 435/40.52; 436/501; 436/503; 436/504; 436/518; 436/63

(58) Field of Classification Search ..................... None
See application file for complete search history.

(56) References Cited

U.S. PATENT DOCUMENTS 6,579,679 B1 * 6/2003 Takagi et al. .................. 435/6

FOREIGN PATENT DOCUMENTS

| EP | 1-078-987 A1 | | 2/2001 |
|----|---|---|---|
| JP | 55-35247 A | | 3/1980 |
| JP | WO99/60122 | * | 11/1999 |
| JP | 2000-37192 A | | 2/2000 |
| WO | WO 9845322 | * | 10/1998 |
| WO | WO 990122 A1 | * | 11/1999 |

OTHER PUBLICATIONS

Kreuzer et al., "Alkaline Phospate . . . Detection with System," Analytica Chimica Acta, vol. 393, 1999 pp. 95-102.
Sato et al., "A Novel Presenilin-2Splice Variant in Human Alzheimer's Disease Brain Tissue," Journal of Neurochemistry, vol. 72, No. 6. 1999, pp. 2498-2505.
Sato et al., Increased Production of . . . Presenilin2,' The Journal of Biological Chemistry, vol. 276, No. 3, Jan. 2001, pp. 2108-2114.
Imaizumi, Kazunori, "Kohatsusci Alzheimer-byo . . . Splicing Ijo," Saishin Igaku, vol. 55, No. 7, 2000 nen, pp. 1641-1648.

* cited by examiner

Primary Examiner—Olga N. Chernyshev
(74) Attorney, Agent, or Firm—Sughrue Mion, PLLC (57) ABSTRACT A method of detecting PS2V characterized by comprising reacting PS2V in a sample with a primary antibody which is bonded to a solid phase and specifically recognizes PA2V, then reacting with a secondary antibody recognizing PS2 or PS2V by any of the following procedures: (a) reacting with a secondary antibody having been enzyme-labeled and recognizing PS2 or PS2V; (b) reacting with a secondary antibody having been biotinylated and recognizing PS2 or PS2V and then reacting with an avidinylated or streptoavidinylated enzyme; (c) reacting with a secondary antibody having been biotinylated and recognizing PS2 or PS2V and then reacting with a biotinylated enzyme and avidin or streptoavidin; and (d) reacting with a secondary antibody recognizing PS2 or PS2V and then reacting with an antibody having been enzyme-labeled and recognizing the secondary antibody; then adding the substrate of the above enzyme and detecting the product formed by the enzyme reaction.

8 Claims, 6 Drawing Sheets

Fig. 1

Fig. 2

| patient | name of disease | sex | age | PS2V(Elisa) |
|---|---|---|---|---|
| 1 | SAH | M |  | 24.7 |
| 2 | NPH | F | 49 | 30.1 |
| 3 | NPH | M | 52 | 31.0 |
| 4 | SAD | F | 74 | 36.7 |
| 5 | SAD | M | 57 | 33.1 |
| 6 | SAD | F | 77 | 34.9 |
| 7 | SAD | M | 65 | 37.2 |

SAH: case of subarachnoid hemorrhage
NPH: case of hydrocephalia
SAD: case of sporadic Alzheimer's disease

CE : counter electrode
RE : reference electrode
WE : working electrode

```
                        SEQUENCE LISTING

<160> NUMBER OF SEQ ID NOS: 9

<210> SEQ ID NO 1
<211> LENGTH: 375
<212> TYPE: DNA
<213> ORGANISM: Homo sapiens

<400> SEQUENCE: 1
atgctcacat tcatggcctc tgacagcgag gaagaagtgt gtgatgagcg gacgtcccta      60
atgtcggccg agagccccac gccgcgctcc tgccaggagg gcaggcaggg cccagaggat     120
ggagagaaca ctgcccagtg gagaagccag gagaacgagg aggacggtga ggaggaccct     180
gaccgctatg tctgtagtgg ggttcccggg cggccgccag gcctggagga agagctgacc     240
ctcaaatacg gagcgaagca cgtgatcatg ctgtttgtgc ctgtcactct gtgcatgatc     300
gtggtggtag ccaccatcaa gtctgtgcgc ttctacacag agaagaatgg acagctttca     360
tccatggctg gttga                                                      375

<210> SEQ ID NO 2
<211> LENGTH: 124
<212> TYPE: PRT
<213> ORGANISM: Homo sapiens

<400> SEQUENCE: 2

Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
```

```
            100                 105                 110
Thr Glu Lys Asn Gly Gln Leu Ser Ser Met Ala Gly
        115                 120

<210> SEQ ID NO 3
<211> LENGTH: 2144
<212> TYPE: DNA
<213> ORGANISM: Homo sapiens

<400> SEQUENCE: 3
gcatttccag cagtgaggag acagccagaa gcaagctatt ggagctgaag gaacctgaga     60
cagaagctag tccccctct gaattttact gatgaagaaa ctgaggccac agagctaaag    120
tgacttttcc caaggtcgcc cagcgaggac gtgggacttc tcagacgtca ggagagtgat    180
gtgagggagc tgtgtgacca tagaaagtga cgtgttaaaa accagcgctg ccctctttga    240
aagccaggga gcatcattca tttagcctgc tgagaagaag aaaccaagtg tccgggattc    300
agacctctct gcggccccaa gtgttcgtgg tgcttccaga ggcagggcta tgctcacatt    360
catggcctct gacagcgagg aagaagtgtg tgatgagcgg acgtccctaa tgtcggccga    420
gagccccacg ccgcgctcct gccaggaggg caggcagggc ccagaggatg agagaacac    480 tgcccagtgg agaagccagg agacgagga ggacggtgag gaggaccctg accgctatgt    540
ctgtagtggg gttcccgggc ggccgccagg cctggaggaa gagctgaccc tcaaatacgg    600
agcgaagcac gtgatcatgc tgtttgtgcc tgtcactctg tgcatgatcg tggtggtagc    660
caccatcaag tctgtgcgct tctacacaga gaagaatgga cagctcatct acacgacatt    720
cactgaggac acaccctcgg tgggccagcg cctcctcaac tccgtgctga cacccctcat    780
catgatcagc gtcatcgtgg ttatgaccat cttcttggtg gtgctctaca gtaccgctg    840 ctacaagttc atccatggct ggttgatcat gtcttcactg atgctgctgt cctcttcac    900 ctatatctac cttggggaag tgctcaagac ctacaatgtg ccatggact accccaccct    960 cttgctgact gtctggaact tcggggcagt gggcatggtg tgcatccact ggaagggccc   1020
tctggtgctg cagcaggcct acctcatcat gatcagtgcg ctcatggccc tagtgttcat   1080
caagtacctc ccagagtggt ccgcgtgggt catcctgggc gccatctctg tgtatgatct   1140
cgtggctgtg ctgtgtccca aagggcctct gagaatgctg gtagaaactg cccaggagag   1200
aaatgagccc atattccctg ccctgatata ctcatctgcc atggtgtgga cggttggcat   1260
ggcgaagctg gaccctcct ctcagggtgc cctccagctc ccctacgacc cggagatgga   1320
agaagactcc tatgacagtt ttggggagcc ttcatacccc gaagtctttg agcctccctt   1380
gactggctac ccaggggagg agctggagga agaggaggaa agggcgtga gcttggcct    1440 cggggacttc atcttctaca gtgtgctggt gggcaaggcg gctgccacgg gcagcggga    1500 ctggaatacc acgctggcct gcttcgtggc catcctcatt ggcttgtgtc tgaccctcct   1560
gctgcttgct gtgttcaaga aggcgctgcc cgccctcccc atctccatca cgttcgggct   1620 catctttttac ttctccacgg acaacctggt gcggccgttc atggacaccc tggcctccca   1680
tcagctctac atctgaggga catggtgtgc acaggctgc aagctgcagg gaattttcat   1740
tggatgcagt tgtatagttt tacactctag tgccatatat ttttaagact tttctttcct   1800
taaaaaataa agtacgtgtt tacttggtga ggaggaggca gaaccagctc tttggtgcca   1860
gctgtttcat caccagactt tggctcccgc tttggggagc gcctcgcttc acggacagga   1920
agcacagcag gtttatccag atgaactgag aaggtcagat tagggcgggg agaagagcat   1980
```

```
ccggcatgag ggctgagatg cgcaaagagt gtgctcggga gtggcccctg gcacctgggt    2040
gctctggctg gagaggaaaa gccagttccc tacgaggagt gttcccaatg ctttgtccat    2100
gatgtccttg ttattttatt gcctttagaa actgagtcct gttc                    2144

<210> SEQ ID NO 4
<211> LENGTH: 2002
<212> TYPE: DNA
<213> ORGANISM: Homo sapiens

<400> SEQUENCE: 4
gcatttccag cagtgaggag acagccagaa gcaagctatt ggagctgaag gaacctgaga      60
cagaagctag tcccccctct gaattttact gatgaagaaa ctgaggccac agagctaaag     120 tgactttttcc caaggtcgcc cagcgaggac gtgggacttc tcagacgtca ggagagtgat    180
gtgagggagc tgtgtgacca tagaaagtga cgtgttaaaa accagcgctg ccctctttga    240
aagccaggga gcatcattca tttagcctgc tgagaagaag aaaccaagtg tccgggattc    300
agacctctct gcggccccaa gtgttcgtgg tgcttccaga ggcagggcta tgctcacatt    360
catggcctct gacagcgagg aagaagtgtg tgatgagcgg acgtccctaa tgtcggccga    420
gagccccacg ccgcgctcct gccaggaggg caggcagggc ccagaggatg agagaacac     480 tgcccagtgg agaagccagg agaacgagga ggacggtgag gaggaccctg accgctatgt    540
ctgtagtggg gttcccgggc ggccgccagg cctggaggaa gagctgaccc tcaaatacgg    600
agcgaagcac gtgatcatgc tgtttgtgcc tgtcactctg tgcatgatcg tggtggtagc    660
caccatcaag tctgtgcgct ctacacagaa gaagaatgga cagctttcat ccatggctgg    720
ttgatcatgt cttcactgat gctgctgttc ctcttcacct atatctacct tggggaagtg    780
ctcaagacct acaatgtggc catggactac cccaccctct gctgactgt  ctggaacttc    840 ggggcagtgg gcatggtgtg catccactgg aagggccctc tggtgctgca gcaggcctac    900
ctcatcatga tcagtgcgct catggcccta gtgttcatca agtacctccc agagtggtcc    960
gcgtgggtca tcctgggcgc catctctgtg tatgatctcg tggctgtgct gtgtcccaaa   1020
gggcctctga gaatgctggt agaaactgcc caggagagaa atgagcccat attccctgcc   1080
ctgatatact catctgccat ggtgtggacg gttggcatgg cgaagctgga ccctcctct    1140 cagggtgccc tccagctccc ctacgacccg gagatggaag aagactccta tgacagtttt   1200
ggggagcctt cataccccga agtctttgag cctcccttga ctggctaccc aggggaggag   1260
ctggaggaag aggaggaaag gggcgtgaag cttggcctcg gggacttcat cttctacagt   1320
gtgctggtgg gcaaggcggc tgccacgggc agcggggact ggaataccac gctggcctgc   1380
ttcgtggcca tcctcattgg cttgtgtctg acctcctgc tgcttgctgt gttcaagaag   1440
gcgctgcccg ccctccccat ctccatcacg ttcgggctca tcttttactt ctccacggac   1500
aacctggtgc ggccgttcat ggacaccctg gcctcccatc agctctacat ctgagggaca   1560
tggtgtgcca caggctgcaa gctgcaggga attttcattg gatgcagttg tatagtttta   1620
cactctagtg ccatatattt ttaagacttt tctttcctta aaaataaag tacgtgttta    1680 cttggtgagg aggaggcaga accagctctt tggtgccagc tgtttcatca ccagactttg   1740
gctcccgctt tggggagcgc ctcgcttcac ggacaggaag cacagcaggt ttatccagat   1800
gaactgagaa ggtcagatta gggcggggag aagagcatcc ggcatgaggg ctgagatgcg   1860
caaagagtgt gctcggggagt ggcccctggc acctgggtgc tctggctgga gaggaaaagc   1920
cagttcccta cgaggagtgt tcccaatgct ttgtccatga tgtccttgtt attttattgc   1980
```

-continued

```
ctttagaaac tgagtcctgt tc                                              2002

<210> SEQ ID NO 5
<211> LENGTH: 40
<212> TYPE: DNA
<213> ORGANISM: Artificial Sequence
<220> FEATURE:
<223> OTHER INFORMATION: Sense primer

<400> SEQUENCE: 5
gaattcatgc tcacattcat ggcctctgac agcgaggaag                             40

<210> SEQ ID NO 6
<211> LENGTH: 40
<212> TYPE: DNA
<213> ORGANISM: Artificial Sequence
<220> FEATURE:
<223> OTHER INFORMATION: Anti-sense primer

<400> SEQUENCE: 6
ctcgagtcaa ccagccatgg atgaaagctg tccattcttc                             40

<210> SEQ ID NO 7
<211> LENGTH: 5
<212> TYPE: PRT
<213> ORGANISM: Homo sapiens

<400> SEQUENCE: 7

Ser Ser Met Ala Gly
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic peptide antigen

<400> SEQUENCE: 8

Gly Arg Leu Ser Ser Met Ala Gly
1               5

<210> SEQ ID NO 9
<211> LENGTH: 17
<212> TYPE: PRT
<213> ORGANISM: Artificial Sequence
<220> FEATURE:
<223> OTHER INFORMATION: synthetic peptide antigen

<400> SEQUENCE: 9

Glu Asn Thr Ala Gln Trp Arg Ser Gln Glu Asn Glu Glu Asp Gly Glu
1               5                   10                  15

Glu
```

METHOD OF DETECTING PS2V

TECHNICAL FIELD

The present invention relates to a method of detecting PS2V which is recognized in sporadic Alzheimer's disease by using antigen-antibody reaction.

BACKGROUND ART

With elderly population progressively increasing, a rapid growth of demential patients has become a serious social problem. Alzheimer's disease (AD) is a kind of dementia, and account for about 30% of senile dementia in Japan and more than half in Europe and U.S. AD is a kind of neurodegenerative disease, and its pathological characters include: (1) senile plaques in which A β is accumulated as a principle component are observed between neuronal cells; (2) abnormal phosphorylated tau protein aggregates in neuronal cells and fibrotic neurofibril are observed; (3) the cerebrum shrinks (deciduation of cerebral neocortex and neuronal cells of hippocampal). As the clinical characters, AD is a progressive dementia presenting hypergasia in general cognition, notably disorder of memory.

AD is classified into familial Alzheimer's disease (FAD), which is small in the number of cases and shows autosomal dominant inheritance, and sporadic Alzheimer's disease (SAD), which apparently lacks family medical history and accounts for 90% of the total Alzheimer's disease. As genes causative of FAD, are identified amyloid precursor protein (APP) gene located on chromosome 21, presenilin-1 (PS1) gene found on chromosome 14 and presenilin-2 (PS2) gene located on chromosome 1. The mechanism of development of FAD has been gradually becoming clear. On the other hand, SAD which makes up a majority of AD cases presents the same neuropathological observations as FAD, but its development mechanism is unknown in a considerable number of aspects.

For common clinical diagnosis of AD, cognition tests such as SM-IV, NINCDS-ADRDA and the like which are proposed in the United State are utilized. However, it is difficult to diagnose extremely slight cognition impediment in an early stage of AD as dementia using conventional cognition tests. The currently used definite diagnosis of AD consists of recognizing deposition of amyloid protein (senile plaques) and accumulation of tau protein (neurofibrillary tangles) in postmortem brain. Thus effective antemortem early diagnostic methods have not been established. In the present circumstances, it is too late when typical symptoms of AD (specific demential symptoms such as incapability of cognition and the like) are recognized.

At present, several kinds of anti-dementia medicines are distributed in a lot of countries, and donepezil has been clinically used in Japan since 1999. These medicines often have a beneficial effect on early-stage cases. Since the medicines are expected to exhibit beneficial effect if AD is diagnosed early, there is a demand for development of a diagnostic marker effective for early treatment of AD.

It has been reported that mRNA of a splicing variant (PS2V) of a PS2 gene with deletion of its fifth exon are observed manifesting frequently in about 70% of the encephala of SAD patients (J. Neurochem., Vol. 72, No. 6, 1999, 2498-2505). The mRNA of PS2V codes for a protein consisting of 124 amino acids having 5 amino acids (Ser-Ser-Met-Ala-Gly) (SEQ ID NO:7) added to 119 amino acid residues (Met1 to Leu119) at the N tenninal of PS2.

Immunohistologic detection of PS2V using samples of CA1 regions of the hippocampi of the encephala of SAD patients have confirmed 100% manifestation of PS2V (J. Biol Chem, 2001 Jan. 19; 276(3):2108-2114).

In vitro analysis has shown that ① in human neuroblastoma SK-N-SH cells in which PS2V is forced to expressed, susceptibility to endoplasmic reticulum (ER) stress increases since the induction of stress responsive protein GRP78 is suppressed; that ② PS2V inhibits autophosphorylation of Ire1 protein (ER stress sensor) and inactivates ER stress response, thereby causing the suppression on the expression of GRP78; and that ③ in cells expressing PS2V, the production of both Aβ1-40 and Aβ1-42 is increased. From these three points, it is considered that in SAD, the expression of PS2V may possibly trigger neuronal death and increasing of Aβ production.

Accordingly, it is considered that highly sensitive detection of PS2V leads to early diagnosis of AD since the expression of PS2V plays an important role in AD development.

As the detection of PS2V, mention may be made of the detection of PS2V itself and the detection of mRNA of PS2V. For early diagnosis, it is impossible to collect a brain tissue of the encephalon of a patient. Therefore, it is necessary to carry out a test using a body fluid of a patient such as cerebrospinal fluid, blood, serum, urine or the like which can be collected relatively easily. However, mRNA is retained in cerebrospinal fluid or serum only for such an extremely short time and is decomposed so quickly that the diagnosis by detecting mRNA is impossible. On the other hand, PS2V is retained in cerebrospinal fluid or serum for a long time as compared with mRNA, and therefore, it is considered suitable for the diagnosis. However, since only a trace amount of PS2V is present in cerebrospinal fluid or serum, a method of detecting PS2V with high sensitivity is required.

Japanese Unexamined Patent Application Publication NO. 2000-37192 has already disclosed a method of producing PS2V by inducing the expression of an abnormal splicing varient of the PS2 gene using oxidative stress loading and β-amyloid stimulation in a culture system of neuronal cells. However, highly sensitive detection of PS2V has not been found.

Conventionally, alkaline phosphatase (referred to as ALP hereinafter) is often used as a labeling molecule in enzyme immunoassay and nucleic acid detection. Since ALP hydrolyzes a substrate which is a phosphate ester, the quantity of an object biomolecule conjugated with ALP can be determined by determining the quantity of a product obtained by hydrolysis with ALP.

Depending upon different determination techniques for the product, the detection of the product is classified into four types, i.e., absorptiometric detection, chemoluminescent detection, fluorescent detection and electrochemical detection.

Literature such as Analytica Chemica Acta 393 (1999) 95-102 and others have reported electrochemical detection using p-methoxyphenyl phosphoric acid as a substrate for ALP. However, methods of highly sensitive detection of PS2V using these substrates have not been found.

Accordingly, there are desired a method of highly sensitive detection of PS2V which is applicable to early diagnosis of AD and a substrate for a conjugating enzyme usable for the method.

DISCLOSURE OF INVENTION

The present invention provides a method of detecting PS2V characterized by comprising:

reacting PS2V in a sample with a primary antibody which is immobilized to a solid phase, executing any one of the following steps (a) to (d):

(a) reacting the PS2V with a secondary antibody which is marked with a label;

(b) reacting the PS2V with a biotinylated secondary antibody, followed by reaction with an avidinated or streptoavidinated label;

(c) reacting the PS2V with a biotinylated secondary antibody, followed by reaction with a biotinylated label and avidin or streptoavidin; and (d) reacting the PS2V with a secondary antibody, followed by reaction with an antibody which is marked with a label and recognizes the secondary antibody; and subsequently, determining the amount of the label captured by the solid state.

Here, the combination of the primary and secondary antibodies may be either one of the following sets (a) and (b).

(a) The primary antibody which specifically recognizes PS2V and the secondary antibody which recognizes PS2 or PS2V.

(b) The primary antibody which recognizes PS2 or PS2V and the secondary antibody which specifically recognizes PS2V.

When a label is an enzyme, suitably used is a method of detecting PS2V characterized by comprising:

reacting PS2V in a sample with a primary antibody which is immobilized to a solid phase and specifically recognizes PS2V, executing any one of the following steps (a) to (d):

(a) reacting the PS2V with a secondary antibody which is labeled with an enzyme and recognizes PS2 or PS2V;

(b) reacting the PS2V with a biotinylated secondary antibody which recognizes PS2 or PS2V, followed by reaction with an avidinated or steptoavidinated enzyme;

(c) reacting the PS2V with a biotinylated secondary antibody which recognizes PS2 or PS2V, followed by reaction with a biotinylated enzyme and avidin or streptoavidin; and (d) reacting the PS2V with a secondary antibody which recognizes PS2 or PS2V, followed by the reaction with an antibody which is conjugated with an enzyme and recognizes the secondary antibody; and subsequently, adding a substrate for the enzyme and detecting a product generated by enzymatic reaction.

Alternatively, the present invention provides a method of detecting PS2V characterized by comprising:

executing any one of the following steps (a) to (d) in the presence of PS2V derived from a sample and a certain amount of PS2V immobilized to a solid state;

(a) reacting PS2V with a primary antibody which is marked with a label and specifically recognizes PS2V;

(b) reacting PS2V with a biotinylated primary antibody which specifically recognizes PS2V, followed by reaction with an avidinated or streptoavidinated label;

(c) reacting PS2V with a biotinylated primary antibody which specifically recognize PS2V, followed by reaction with a biotinylated label and avidin or streptoavidin; and (d) reacting PS2V with a primary antibody which specifically recognizes PS2V, followed by reaction with a secondary antibody which is marked with a label and recognizes the primary antibody; and subsequently determining the amount of the label captured by the solid state and detecting the PS2V derived from the sample by calculation from the certain amount of the primary antibody and the determined amount of the label.

The present invention further provides a method of detecting PS2V characterized by comprising:

reacting a certain amount of an antibody which is immobilized to a solid phase and specifically recognizes PS2V with PS2V derived from a sample and a certain amount of PS2V marked with a label in competition against each other;

determining the amount of the label captured by the solid phase; and detecting the PS2V derived from the sample by calculation from the certain amount of the antibody and the determined amount of the label.

BRIEF DESCRIPTION OF DRAWINGS

FIG. 1 shows the result of Example 1 of the present invention in which chemoluminescent was determined by sandwich method using rGST-PS2V as a sample;

FIG. 2 shows the result of the present invention of determination of PS2V in cerebrospinal fluid of patients of subarachnoid hemorrhage, hydrocephalia and sporadic Alzheimer's disease;

FIG. 3 shows the result of Example 1 of the present invention in which absorbance was determined by sandwich method using rGST-PS2V as a sample;

FIG. 4 shows the construction of FIA-EC-DT used in electrochemical detection according to the present invention;

FIG. 5 shows the construction of an FIA-EC-DT detector according to the present invention;

FIG. 6 shows the result of Example 2 of the present invention in which electrochemical detection was carried out by sandwich method using rGST-PS2V as a sample (dependency upon the amount of an antigen, an average value of the detection repeated three times);

FIG. 7 shows the result of Example 2 of the present invention in which electrochemical detection was carried out by sandwich method using rGST-PS2V as a sample (values are obtained by deducting a background value obtained with no antigen used);

FIG. 8 shows the result of Example 3 of the present invention in which absorbance was determined by competitive assay using rGST-PS2V as a sample;

FIG. 9 shows the results of Example 4 of the present invention in which electrochemical detection was carried out by competitive assay using rGST-PS2V as a sample.

BEST MODE FOR CARRYING OUT THE INVENTION

PS2V (SEQ.ID.NO. 1) to be detected according to the present invention is a polypeptide derived from a splicing variant of presenilin-2 which lacks exon 5. PS2V has an amino acid sequence represented SEQ ID NO: 2 or an amino acid sequence including addition, deletion or substitution of one to several amino acids with respect to the amino acid sequence of SEQ ID NO: 2. The number of amino acids which may be added, deleted or substituted is generally 1 to about 20, preferably 1 to about 10, and more preferably 1 to about 5. Such a polypeptide generally has about 80% or more, preferably 90% or more, more preferably 95% or more homology with the amino acid sequence of SEQ ID NO:2.

The normal PS2 gene has a cDNA sequence represented by SEQ ID NO: 3, and the cDNA sequence corresponding to the splicing variant (PS2V) gene lacking exon 5 (exons 4 and 6 are connected) is shown in SEQ.ID.NO. 4. In the base sequence of SEQ ID NO: 4, the junction site of exon 4 with exon 6 lies between bases 705th and 706th. The base sequence of SEQ ID NO: 1 corresponds to bases 359th to 724th of SEQ.ID.NO. 4. SEQ ID NOs: 1 to 4 are disclosed in Japanese Unexamined Patent Publication No. 2000-37192.

Samples used according to the present invention may preferably be body fluid samples such as cerebrospinal fluid, serum and the like.

The antibody which specifically recognizes PS2V means an antibody which does not recognize PS2 but recognizes PS2V. The antibody recognizes a region including the amino acid sequence of Ser-Ser-Met-Ala-Gly at the C-terminal of the amino acid sequence of SEQ ID NO: 2.

The antibody which recognizes PS2 or PS2V means an antibody which recognizes an amino acid sequence common to PS2 and PS2V, for example, an antibody which recognizes amino acid residues 42nd to 58th of the amino acid sequence of PS2.

These antibodies can be obtained by preparing a peptide including Ser-Ser-Met-Ala-Gly (SEQ ID NO:7) and a peptide including amino acid residues 42nd to 58th of the amino acid sequence of PS2, immunizing rabbits or the like with these peptides for a certain period of time and collecting serum from the rabbits according to the conventional method.

These antibodies are preferably used in the form of F(ab')$_2$ or Fab' fragments for suppressing non-specific reaction.

For labeling antibody, a radioisotope ($^{125}$I), the enzymes, fluorescent and luminous molecule (a dye such as fluoresceine, fluorescent protein such as GFP, a complex coordinated to rare earth element, material of organic EL element, and so on), chromophore (photoactive yellow protein: PYP, and so on), and electroactive species (ferrocene, and so on) may be used.

For labeling an antibody with an enzyme, the antibody may be labeled directly with the enzyme to form an enzyme-labeled antibody. Or the antibody may be biotinylated, and then an avidinated (or streptoavidinated) enzyme may be bound to the biotinylated antibody taking advantage of specific bonding of biotin and avidin (streptoavidin). Or the biotinylated antibody may be reacted with avidin (or streptoavidin) and a biotinylated enzyme. Or another antibody which recognizes the antibody and is labeled with the enzyme may be bound to the unlabeled antibody.

In the case where PS2V needs to be detected with high sensitivity, there often arise problems of decline in the activity of the antibody caused by labeling reaction and non-specific adsorption of the enzyme-labeled antibody. Thus, it is important to suppress modification to an antigen-binding site of the antibody and preventing multiplicity of the antibody. For this purpose, the enzyme may be introduced to thiol group of Fab'. More particularly, instead of using a reagent which modifies amino group of the antibody unselectively, a bifunctional hetero-crosslinking agent such as N-succinimidyl-6-maleimidohexanoate may be used to make a composite between amino group of an enzyme and thiol group obtained by reduction of disulfide of the antibody. Further more particularly, IgG is digested with pepsin to remove a highly hydrophobic Fc region and F(ab')$_2$ fragment is collected. The disulfide bonding at a hinge portion is reduced under moderate conditions using 2 mmol/L solution of 2-mercaptoethylamine (0.1 mol/L sodium phosphate buffer containing 5 mmol/L EDTA, pH6.0, 37° C., 90 minutes) to form thiol group, thereby Fab' being prepared. After concentration of Fab', the enzyme-labeled antibody is obtained by reaction with an enzyme to which maleimido group is introduced.

A known enzyme available for labeling can be used as the labeling enzyme. Examples of such enzymes include HRP (horseradish peroxidase), ALP (alkaline phosphatase), β-D-galactosidase, glucose-6-phosphate dehydrogenase, luciferase and the like. A substrate for the enzyme may be selected from light-absorptive substrates, fluorescent substrates and luminous substrates as appropriate according to the enzyme to be used. Examples of such substrates include luminol, o-phenylenediamine(OPD), 3,3',5,5'-tetramethylbenzidine (TMB), 2-nitrophenyl-β-D-galactoside, 4-nitrophenyl-phosphate, 4-methylumbelliferyl-β-D-galactoside, glucose-6-phosphate, 4-hydroxyphenylacetic acid, 3-(4-hydroxyphenyl)propionic acid and the like. In the case where the enzyme is ALP, the substrate therefor may be p-nitrophenyl phosphate (pNPP), phenyl phosphoric acid, aminophenyl phosphate, naphthyl phosphate, 4-methylbelliferyl phosphate, and the like.

Especially in the case where the enzyme is ALP in the present invention, the substrate may preferably be a phosphate ester of a phenol derivative having at least an electron donating group at o-position and/or at p-position, more preferably p-methoxyphenyl phosphate. Examples of the electron donating group include an alkyl, an ether, a silyl and an amino group, and derivatives thereof. Preferably, the electron donating group may be a lower alkoxy group. Further more, using p-methoxyphenyl phosphate is more preferable.

The method of detecting PS2V of the present invention will be described below by giving an example in the case where an antibody which specifically recognizes PS2V is used as the primary antibody, an antibody which recognizes PS2 or PS2V is used as the secondary antibody, and an enzyme is used as a label. In the above description, the measurement may also be carried out in the case that the primary and secondary antibodies are exchanged.

First, the primary antibody which does not react with PS2 but reacts with PS2V (which specifically recognizes PS2V) is immobilized to a solid phase. As the solid phase, may be used a test tube, a 96-well plate, beads and the like. The primary antibody can be immobilized to the solid phase by a known method, for example, by physical adsorption and by chemical binding using a crosslinking agent such as glutaraldehyde, carbodiimide and the like.

After the antibody is immobilized, the solid phase is blocked with use of a blocking agent such as BSA (bovine serum albumin), casein, PVA (polyvinyl alcohol), skim milk, keratin, dextran, gelatin and the like, for preventing non-specific adsorption to the solid phase.

Next, PS2V in a sample is reacted with the primary antibody immobilized to the solid phase at a reaction temperature of about 4 to 40° C., preferably about 4 to 30° C. for a reaction time of about 5 minutes to overnight, preferably for about 40 minutes to 6 hours. By this step, only PS2V is bound to the primary antibody to be captured by the solid phase.

After B/F separation, the resulting PS2V is reacted with the secondary antibody which recognizes PS2 or PS2V. The reaction conditions are the same as those for the primary antibody. The secondary antibody may be conjugated directly with an enzyme as described above. Or the biotinylated labeled antibody may also be reacted with an avidinated (or streptoavidinated) enzyme to form an enzyme-labeled antibody.

The biotinylated secondary antibody may also be reacted with avidin (or streptoavidin) and a biotinylated enzyme to form an enzyme-conjugated antibody. Alternatively, the PS2V is reacted with the secondary antibody, unlabeled, and then with an enzyme-labeled antibody which recognizes the secondary antibody, which may be allowed to react for enzyme-labeling.

Next, a substrate for enzyme is added and allowed to react with the enzyme. Then, a product generated by enzymatic reaction is detected. Suitable reaction conditions including adequate reaction temperature and appropriate reaction time may be varied depending upon a combination of an enzyme and a substrate to be used. For example, the cases where HRP is used as the enzyme are explained as follows. (1) If OPD is used as the substrate, the reaction of the enzyme with OPD is carried out using, as a reaction buffer, a 0.05 M citrate-phosphate buffer (pH 5.0) containing 0.4 mg/mL of OPD and 0.012 to 0.02% of hydrogen peroxide, at 20 to 45° C., preferably 24 to 37° C. for 1 minute to 2 hours, preferably 10 minutes to 1 hour. The reaction is stopped with a 3N hydrochloric acid or 3M sulfuric acid in an amount one-quarter as much as the amount of solution containing the substrate. The absorbance at 490 nm is determined: (2) If TMB is used as the substrate, the reaction of the enzyme with TMB is carried out using, as a reaction buffer, a 0.1 M citrate buffer (pH 5.5) containing 0.1 to 0.2 mg/mL of TMB, 0.01 to 0.02% of hydrogen peroxide, 1% of DMF and 0.01% of Tween 20, at 20 to 45° C., preferably 24 to 37° C. for 1 minute to 2 hours, preferably 5 to 30 minutes. The reaction is stopped with a 1M phosphoric acid, hydrochloric acid or sulfuric acid in the same volume as that of solution containing the substrate. The absorbance at 450 nm is determined. (3) If the case where luminol is used as the substrate, the reaction is carried out at 20 to 37° C., preferably 24 to 37° C., for 1 to 30 minutes, preferably 1 to 7 minutes. The resulting product generated by enzymatic reaction can be detected by a spectrophotometer if the product can be detected by its absorbance, by a fluorospectrophotometer if the product can be detected by its fluorescence, by a photometer if the product is a luminous substance, and by an electrochemical detector for detecting current generated when the product is oxidized on an electrode. PS2V can be detected by the presence of the product generated by enzymatic reaction. More specifically, the amount of PS2V can be calculated by a calibration curve of the enzyme reaction product obtained by adding PS2V having known concentrations.

In another embodiment, the sample is mixed beforehand with the secondary antibody and allowed to react for about an hour. A liquid containing the reaction mixture is added to wells of a reaction plate to which the primary antibody has been immobilized and allowed to react with the primary antibody. After B/F separation, the detection can be carried out in the same manner as described above.

PS2V can also be detected by the competitive assay. First, in the case where an antigen is immobilized to a solid phase, a certain amount of PS2V is immobilized to the solid phase by a known method. PS2V used at this time is not particularly limited so long as it includes the variant polypeptide described above. For example, a purified PS2V, a synthetic peptide and a hybrid protein may be used.

Subsequently, a sample is added to a reactor containing the immobilized PS2V. A certain amount of an antibody which specifically recognizes PS2V is added to the reactor to bring the PS2V immobilized on the solid phase and PS2V from the sample in competition for reaction. The PS2V immobilized on the solid phase and the PS2V from the sample contend against each other for the antibody. Since the amount of the PS2V immobilized on the solid phase and the amount of the antibody added are fixed, the more the amount of the PS2V from the sample is, the less antibody is bound to the PS2V immobilized on the solid phase. If a blank sample is prepared which does not contain PS2V and the amount of the antibody bound to the PS2V immobilized to the solid phase is measured, the amount of the PS2V in a non-blank sample can be obtained from a decrease in the amount of the antibody bound to the PS2V immobilized to the solid phase. The reaction conditions such as reaction temperature and reaction time are the same as those in the sandwich method. After reaction, the B/F separation is performed to remove PS2V and the antibody which are not bound to the PS2V immobilized to the solid phase. Subsequently, in the case where a labelled antibody is used as the antibody, PS2V is detected by determining the label amount. In the case where a biotinylated antibody is used, the antibody is conjugated using an avidinated (or streptoavidinated) label. Alternatively, PS2V is reacted with an antibody specifically recognizing PS2V and the antibody is conjugated with labeled antibody which recognizes the antibody specifically recognizing PS2V. PS2V can be detected by measuring the label amount. For labeling, the above-mentioned materials may be used.

Second, in the case where the antibody is immobilized to the solid phase, a certain amount of the antibody which specifically recognizes PS2V is immobilized to the solid phase by a known method. A labled PS2V is prepared. PS2V used at this time is not particularly limited so long as it includes the variant polypeptide described above. For example, a purified PS2V, a synthetic peptide and a hybrid protein may be used. PS2V can be conjugated by a known protein labeling technique. Usable labels are the same as described above.

Further, in a reactor in which a certain amount of the antibody which specifically recognizes PS2V is immobilized, a certain amount of a labeled PS2V and a sample containing an unknown amount of PS2V are fed so that the labeled PS2V and the PS2V from the sample contend against each other for the antibody. Since the amount of the antibody immobilized on the solid phase and the amount of the labeled PS2V are fixed, the more the PS2V comes from the sample, the less labeled PS2V is bound to the antibody immobilized on the solid phase. If the amount of the labeled PS2V bound to the antibody immobilized on the solid phase is obtained by determining a blank sample not containing PS2V, the amount of PS2V in the sample can be obtained from a decline in the amount of the labeled PS2V bound to the antibody immobilized on the solid phase. The reaction conditions such as the reaction temperature and the reaction time are the same as those for the sandwich method. After reaction, the B/F separation is conducted to remove the labeled PS2V unbound to the solid phase. Subsequently, PS2V can be detected by determining the amount of the labeled PS2V captured by the solid phase.

Examples in which an antibody which specifically recognizes PS2V is used as the primary antibody and an antibody which recognizes PS2 or PS2V is used as the secondary antibody will be hereinafter described in detail, but the present invention is not limited thereto.

Preparation of Primary Antibody (Rabbit Anti-SSMAG Antibody)

Cysteine residue was added at the N-terminal of a synthetic peptide, Gly-Arg-Leu-Ser-Ser-Met-Ala-Gly (SEQ ID NO:8). The SH group of the cysteine residue was conjugated with amino group of hemocyanin (KLH) using m-maleimidobenzoyl-N-hydroxysuccinimide ester according to the conventional method (see Biochemistry, 18, 690-697 (1979)). The resulting conjugates were immunized subcutaneously in the backs of rabbits to prepare an antiserum. An antibody was purified by an affinity column cross-linked with the peptide. The antibody against the peptide was prepared by SAWADY Technology Co., Ltd.

Preparation of Secondary Antibody (Rabbit Anti-PS2N Antibody: Anti PS2N Ab)

Cysteine residue was added at the N-terminal of a synthetic peptide, Glu-Asn-Thr-Ala-Gln-Trp-Arg-Ser-Gln-Glu-Asn-Glu-Glu-Asp-Gly-Glu-Glu (amino acids 42nd to 58th of the amino acid sequence of PS2) (SEQ ID NO:9). The SH group of the cysteine reside was conjugated with amino group of hemocyanin (KLH) using m-maleimidobenzoyl-N-hydroxysuccinimide ester according to the conventional method. The resulting conjugates were immunized subcutaneously in the backs of rabbits to prepare an antiserum. An antibody was purified by an affinity column cross-linked with the peptide. The antibody against the peptide was prepared by SAWADY Technology Co., Ltd.

Biotinylation of Secondary Antibody

The Anti-PS2N Ab (372.1 µg/mL) prepared as described above, 1 mL, was added to Centricon YM30 (Cut-off=30000 Da, produced by Amicon). The resulting mixture was centrifuged at 4500 rpm at 4° C. for 30 minutes and concentrated to 100 µL. PBS(−), 1.5 mL, was added, and centrifugation was performed under the same conditions for concentration. The resulting mixture was measured up to 500 µL.

The above obtained Anti-PS2N Ab solution, 500 µL, was passed through an NAP-5 column (produced by Amersham Pharmacia Biotech) equilibrated with 10 mL of PBS(−). After 500 µL of eluate were disposed of, 1 mL of eluate (fraction containing the antibody) was collected. The absorbance $A_{280}$ of the fraction was determined (absorbance index $\epsilon$=1.4 mL/mg·cm) to calculate the concentration of the antibody (antibody concentration=282.4 µg/ml).

Next, a biotinylating reagent, EZ-Link Sulfo-NHS-LC-Biotin (sulfosuccinimidyl-6-(biotinamido)hexanoate, produced by Pierce Biotechnology, Inc.), was added to the antibody solution in the proportion of biotinylating reagent: IgG=54 mol:1.3 mol=42:1 and allowed to react at 4° C. for 2 hours. Subsequently, the solution containing the reaction product, 1 mL, was added to Centricon YM30 and was centrifuged at 4500 rpm at 4° C. for 30 minutes and concentrated to 100 µL. TBS, 1.5 mL, was added, and centrifugation and concentration were performed twice under the same conditions for removing the unreacted biotinylating reagent. The absorbance $A_{280}$ was determined (absorbance index $\epsilon$=1.4 mL/mg·cm) to calculate the concentration of the antibody (antibody concentration=378.83 µg/ml).

Preparation of Genetically Recombined GST-PS2V (r GST-PS2V)

(1) Human Neuronal Cell Culture and Preparation of RNA

Human neuroblastoma SK-N—S cells (ATCC HTB-11) were cultured in an α-MEM medium (α-Minimum Essential Medium, produced by GIBCO-BRL) containing 10% v/v fetal bovine serum in a culture dish of 10 cm diameter in a $CO_2$ incubator at 37° C. for about 48 hours up to a confluent state, then the medium was replaced with the α-MEM medium not containing the fetal bovine serum, and cultured for about 2 hours.

The culture dish was transferred into an oxygen-poor incubator (oxygen concentration of 1% or less, 95% $N_2$, 5% $CO_2$) (produced by Coy Laboratory Products, Inc.), and the cultured cells were further cultured for 16 hours.

The thus cultured cells were collected and washed with phosphate buffered saline (PBS). The resulting cells were suspended in 700 µL of a buffer for cytolysis (RLT solution, produced by QIAGEN K.K.) and were comminuted to obtain a cell extract. Total RNA was prepared from the cell extract using an RNA preparation kit (Trade name: RNeasy total RNA kit, produced by QIAGEN).

(2) Preparation of cDNA of PS2V

Using the obtained RNA (total RNA, 1 µg) as a template, single-stranded cDNA was synthesized in a 0.05 mL of a buffer (0.05M Tris-HCl, pH8.3, 0.075M KCl, 0.003M $MgCl_2$, DTT, 0.0002M deoxynucleotides) containing oligo dT primer (50 pmole), random oligonucleotide (5 pmole) and reverse transcriptase (produced by Promega Corporation, Moloney leukaemia virus reverse transcriptase) (200 units) by one hour's reaction at 42° C.

(3) Preparation of Vector

Primers were designed at 5' and 3' terminals of the PS2V gene so that the PS2V gene could be inserted in a multi-cloning site of vector p GEX-4T-1 (produced by Amersham Pharmacia Biotech) in an in-frame state. The primers are a sense primer whose sequence is 5'-GAA TTC ATG CTC ACA TTC ATG GCC TCT GAC AGC GAG GAA G-3' (SEQ ID NO: 5) and an anti-sense primer whose sequence is 5'-CTC GAG TCA ACC AGC CAT GGA TGA AAG CTG TCC ATT CTT C-3' (SEQ ID NO: 6). The single-stranded DNA obtained above was used for PCR (reaction of denaturation at 95° C. for 30 seconds, reaction of elongation at 72° C. for a minute, and annealing at 55° C. for 30 seconds, 30 cycles) to prepare and isolate gene fragments. The gene fragments were cut with restriction enzymes EcoRI and XhoI. Likewise, EcoRI and XhoI sites were cut out of p GEX-4T-1.

Next, the isolated PS2V gene fragments were purified, and were ligated with p GEX-4T-1 treated as described above to introduce the PS2V gene into the multi-cloning site of p GEX-4T-1. A DNA sequencer was used to ensure that the obtained product was a plasmid p GEX-4T-1/PS2V having a proper sequence. The ligation was carried out using a ligation kit (trade name: DNA Ligation Kit Ver. 2, produced by TaKaRa Bio Inc.).

(4) Expression of rGST-PS2V

The expression vector of rGST-PS2V prepared as described above was transformed into JM109 competent cells (*Escherichia coli*) and cultured on an LB medium plate. PCR confirmed the introduction of the vector in emerged colonies.

Subsequently, the colonies were cultured in a liquid LB medium containing 100 µg/mL of sodium ampicillin overnight.

The resulting culture liquid, 2 mL, was added to 200 mL of an LB medium. IPTG (isopropyl-β-D-thiogalactopyranoside) was added to induce the expression of the fused protein so that the final concentration became 0.1 mM after 2 hours at 37° C.

After two hours, bacterial cells were collected. The culture liquid, 50 mL, was centrifuged at 8000 rpm at 4° C. for 10 minutes and deposit was collected. The collected deposit was suspended in 3 mL of PBS containing phenylmethylsulfonyl fluoride in a final concentration of 1 mM, and the resulting suspension was ice-cooled and the bacterial cells were sonicated. After centrifugation (at 15000 rmp at 4° C. for 10 minutes), supernatant was collected.

Subsequently, the collected supernatant was added to a column of a glutathione sepharose 4B (produced by Amersham Pharmacia Biotech). After washing with 50 mM Tris-HCl (pH7.4), rGST-PS2V was eluted with a 10 mM reduced glutathione solution. The absorbance of each fraction collected was determined, and a fraction showing a large absorbance at $A_{280}$ was subjected to electrophoresis to confirm the presence of rGST-PS2V. After removing glutathione by dialysis, the protein concentration was measured using Bio-Rad DC Protein Assay (produced by Bio-Rad Laboratories, Inc.). This fraction was used as rGST-PS2V standard.

EXAMPLES

Example 1

Detection of rGST-PS2V by the Sandwich Method (Using HRP and Luminal)

(1) Immobilization of Primary Antibody to Solid Phase

The primary antibody prepared as described above was added to a 96-well plate (Cliniplate, produced by Labsystems, Inc.) by 1 pmol/well and allowed to stand at 37° C. for an hour. The 96-well plate was washed with TBS-T (50 mM Tris-HCl 150 mM NaCl 0.05% w/v Tween 20(pH7.4)) containing 0.5% w/v Block Ace (produced by Dai Nippon Pharmaceutical Co., Ltd.) by 0.32 mL/well three times. A TBS solution (50 mM Tris-HCl 150 mM NaCl(pH7.4)) containing 25% w/v Block Ace was added by 300 µL/well and allowed to stand at 37° C. for an hour for blocking.

(2) Determination of Chemoluminescence of rGST-PS2V

Solutions of normal serum containing 0 to 31 pmol of rGST-PS2V were added to the plate prepared as described above by 50 µL/well and allowed to react at 37° C. for an hour. After reaction, the plate was washed with TBS-T containing 0.5% w/v Block Ace by 0.32 mL/well three times for B/F separation.

Subsequently, the biotinylated secondary antibody prepared as described above was added by 0.3 pmol/well and allowed to react at 37° C. for an hour. After reaction, the plate was washed with TBS-T containing 0.5% w/v Block Ace by 0.32 mL/well three times. A solution of TBS-T containing a 5000-fold dilution of streptoavidin-HRP (produced by Zymed Laboratories, Inc.) and 0.5% w/v Block Ace was added by 50 µL/well and allowed to react at 37° C. for an hour. After reaction, the plate was washed with TBS-T containing 0.5% w/v Block Ace by 0.32 mL/well three times.

Figure 1:
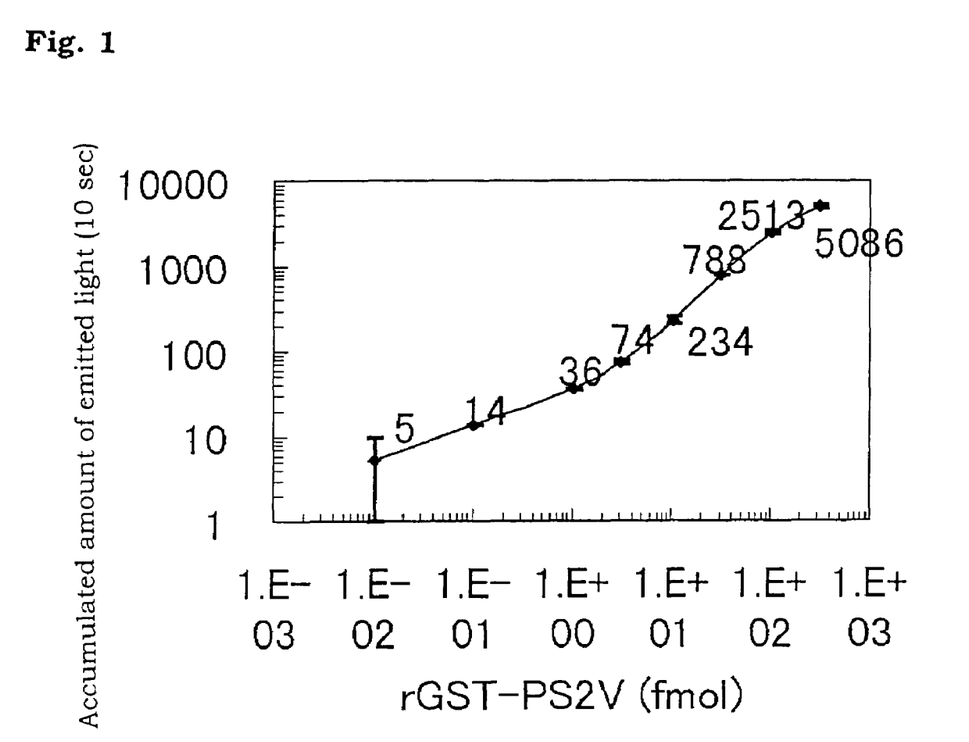

Subsequently, luminol (Super Signal ELISA Pico, produced by Pierce Biotechnology, Inc.), which is a luminescent substrate, was added by 80 µL/well and allowed to react at 30° C. for 5 minutes. When five minutes passed from the beginning of enzymatic reaction, the accumulated amount of light emitted for 10 seconds was measured using Labsystems Luminoskan (produced by Dai Nippon Pharmaceutical Co., Ltd.). As shown in FIG. 1, a quantifiability in an amol ($10^{-18}$ mol) order was obtained.

Measurement on SAD Patient Cerebrospinal Fluid

Figure 2:
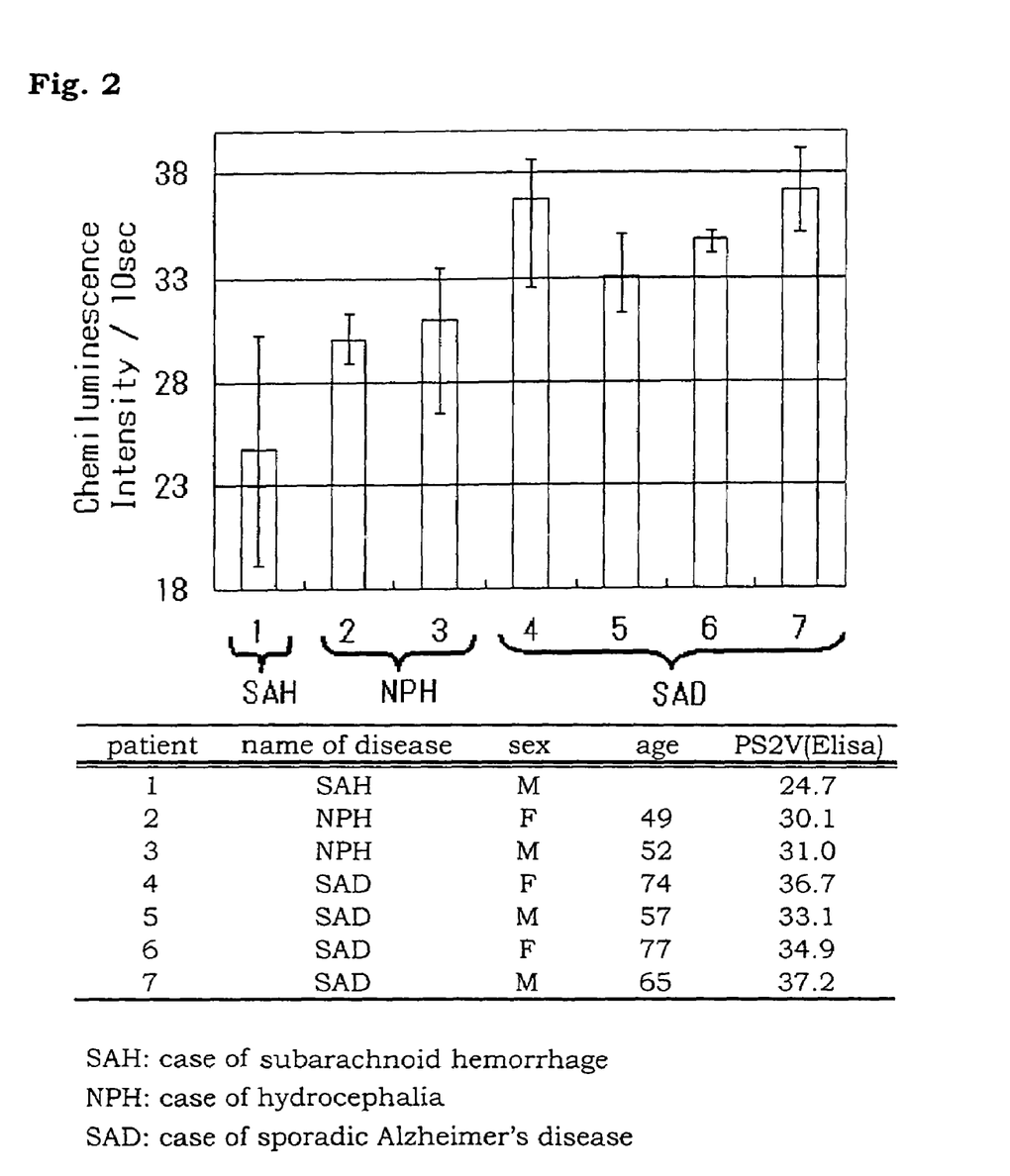

Measurement of PS2V was carried out on samples of 4 cases of SAD, 1 case of subarachnoid hemorrhage and 2 cases of hydrocephalia in the same manner as described above. FIG. 2 shows the results, which confirm that the measurement resulted in higher values with the SAD cases than with the other cases and could provide an indication for diagnosis of SAD.

Determination of Absorbance of rGST-PS2V

Figure 3:
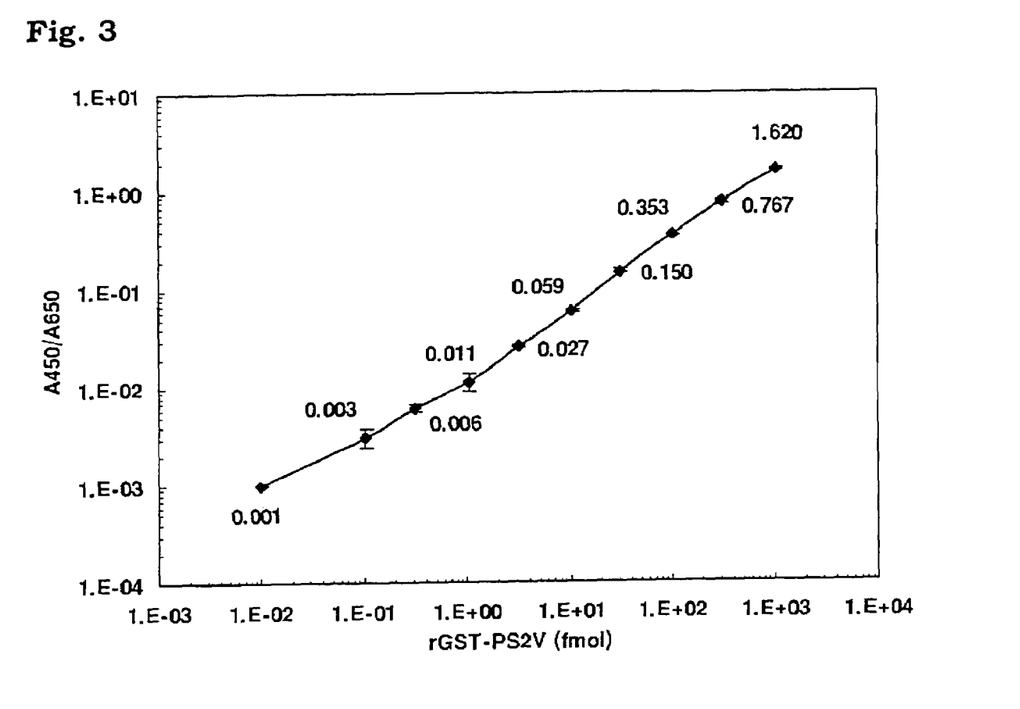

Antigen-antibody reaction was conducted in the same manner as described above except that the primary antibody prepared as described above was added to a 96-well plate (ELISA Plate, produced by IWAKI Glass Co.) by 3 pmol/well. Enzymatic reaction was started by adding TMB (produced by KPL) as a substrate by 100 µL/well and continued at 30° C. for 15 minutes. Fifteen minutes after the start of the enzymatic reaction, 1M $H_3PO_4$ was added by 100 µL/well. The absorbance at 450 nm was determined with background correction in absorbance between 450 nm and 650 nm using VERSAmax tuneable microplate reader (produced by Molecular Devices). FIG. 3 shows average absorbance. Like the determination of chemoluminescence, a quantifiability in an amol ($10^{-18}$ mol) order was obtained.

Example 2

Detection of rGST-PS2V by Sandwich Method (Using ALP and pMPP (p-methoxyphenyl phosphoric acid))

(1) Immobilization of Primary Antibody to Solid Phase

The rabbit anti-SSMAG antibody (the primary antibody) prepared as described above was added to a 96-well plate (Cliniplate, produced by Labsystems, Inc.) by $6.25 \times 10^{-11}$ mol/well and allowed to stand at 37° C. for an hour. The 96-well plate was washed with TBS-T (50 mM Tris-HCl 150 mM NaCl 0.05% w/v Tween 20(pH7.4)) containing 0.1% w/v BSA (A6003, produced by SIGMA) by 300 µL/well three times. A TBS-T solution containing 3% w/v BSA was added by 305 µL/well and allowed to stand at 37° C. for an hour for blocking.

(2) Determination of rGST-PS2V by Electrochemical Detection

Onto the plate prepared as described above, a normal serum solution containing $1 \times 10^{-17}$ to $1 \times 10^{-12}$ mol of rGST-PS2V was added by 50 µL/well and allowed to react at 37° C. for an hour. After reaction, the plate was washed with TBS-T containing 0.1% w/v BSA by 300 µL/well three times for B/F separation.

Next, the biotinylated secondary antibody (rabbit anti-PS2N antibody) prepared as described above was added by $3.12 \times 10^{-13}$ mol/well and allowed to react at 37° C. for an hour. After reaction, a TBS solution (50 mM Tris-HCl 150 mM NaCl(pH7.4)) containing 3% w/v BSA (A6003, produced by SIGMA) was added by 305 µL/well and allowed to stand at 37° C. for an hour for blocking. After the plate was washed with TBS-T containing 0.1% w/v BSA by 0.32 mL/well three times. Then a TBS-T solution containing a 5000-fold dilution of streptoavidin-ALP (produced by DAKO, Japan Co., Ltd) and 0.5% w/v Block Ace was added by 50 µL/well and allowed to react at 37° C. for an hour. After reaction, the plate was washed with TBS-T containing 0.1% w/v BSA by 300 µL/well three times.

Next, 10 mM solution of pMPP (produced according to the method described in Analytica Chimica Acta 393 (1999)

Figure 4:
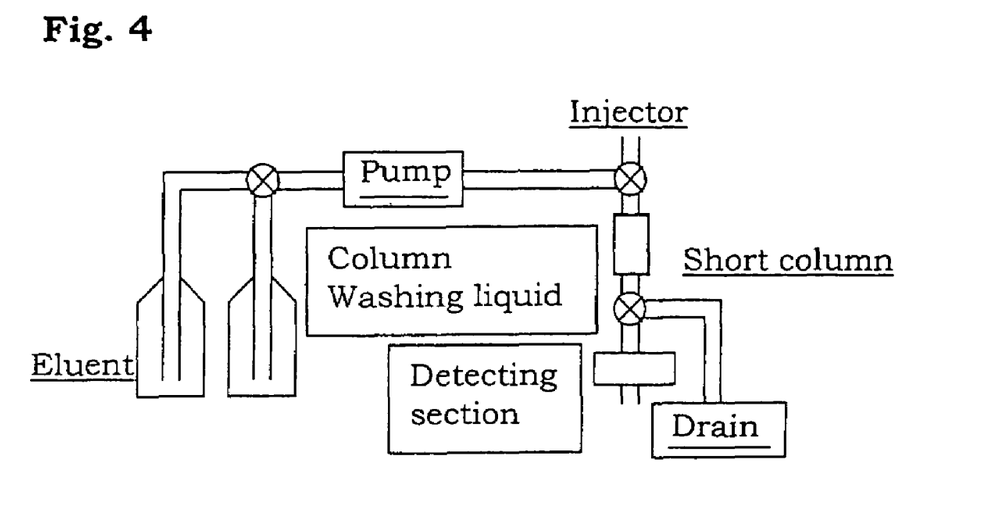

95-102, by Tanabe R&D) in 0.5M CB-Buffer was added as a substrate by 90 μL/well, and further, 20 μL of 0.1M Mg(ClO$_4$)$_2$, 10 μL of 0.5M CB-Buffer (pH9.5) and 60 mL of RO water were added, followed by reaction at 37° C. for 30 minutes. Thereafter, 45 μL of a 0.6M EDTA-3Na solution (adjusted to pH9.5 using NaOH) at 0° C. to stop enzymatic reaction. After stopping enzymatic reaction, the mixture in each well was transferred to another plate (ELISA plate, produced by IWAKI).

p-Methoxyphenol produced by hydrolysis of pMPP by ALP was detected using a Flow Injection Analysis-Electro Chemical-Amperometric Detection System (referred to as FIA-EC-DT hereinafter). FIG. 4 shows the construction of the FIA-EC-DT.

The FIA-EC-DT is composed of a degasser (Vacuum Degasser LC-27A), a pump (MICRO LC PUMP LC-100), an injection valve (produced by Reodine, 77251), an ODS column (YMC-Pack-ODS-AM, AM3C7AM 12SO$_5$-L502WT No. 02070458(W)), a short column (YMC semi-micro guard cartridge column 2×10, AM12S05-0102CC) and an electrode detector.

In a fluid path of the FIA-EC-DT, 0.1 M phosphate buffer containing 45% v/v or 50% v/v methanol was passed as eluent. The degasser (Vacuum Degasser LC-27A) removes air bubbles from the eluent. The pump (MICRO LC PUMP LC-100) conveys the eluent to the electrode detector at 250 μL/min. With keeping the eluent being conveyed, the injection valve (produced by Reodine, 77251) was used for injection. In the present invention, 20 μL of the sample to be determined were set to flow in the fluid path of the FIA-EC-DT.

The short column was disposed between the injection valve and the electrode detector for preventing a protein component in the sample from reaching the electrode detector and thereby fouling the surface of the electrode. Besides, noise current caused by the buffer and current of components for detection are separated by the short column at time to reach the detector.

Figure 5:
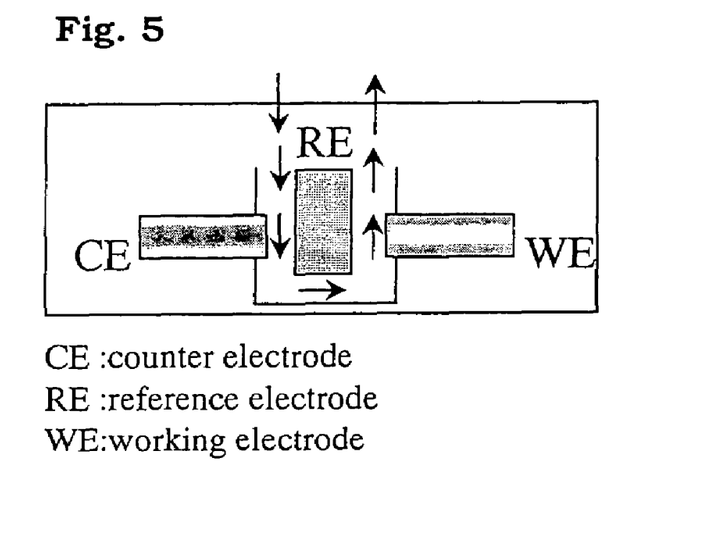

FIG. 5 shows the construction of the electrode detector. Generally, the electrochemical detection requires a working electrode (WE), a reference electrode (RE) and a counter electrode (CE). The working electrode provides an oxidation-reduction potential of a substance to be detected and takes an oxidation-reduction current produced by oxidation-reduction reaction. The reference electrode provides a reference for setting an oxidation-reduction potential of the working electrode. The counter electrode prevents an excess oxidation-reduction current from flowing in the reference electrode at the oxidation-reduction reaction. Generally used electrochemical detection systems include three-electrode systems and four-electrode systems. The three-electrode systems have each of three types of the electrodes, and the four-electrode systems have two working electrodes and each of the other two types of the electrodes. In the present invention, the FIA-EC-DT electrode detector has the three electrode system: The reference electrode was Ag/AgCl (BAS RE-3V); the counter electrode was integrated in a fluid path; and the working electrode was a glassy carbon electrode (BAS 003456) which was a radial flow-type electrode. ALS832a produced by BAS was used as an electrochemical meter.

The substance to be detected was p-methoxyphenol, which was a hydrolytic reaction product of the substrate. Serially diluted solutions 1 nM to 1 μM of p-methoxyphenol (084-01282 (special grade) by Wako Pure Chemical Industries, Ltd., used as it was) in 0.1 M phosphate buffer (pH6.92) were prepared, were each injected into the FIA-EC-DT and was electrochemically detected to obtain a peak value of an oxidation current and produce a calibration curve. As detection conditions, the working electrode potential (oxidation potential) was 0.55 V vs Ag/AgCl, and the appearance time from the injection valve to the electrode detector was 90 seconds.

Under the same detection conditions, samples according to the present Examples after the stopping of the enzymatic reaction were injected into the FIA-EC-DT to obtain the peak value of the oxidation current. The results are shown in FIGS. 6 and 7.

Figure 6:
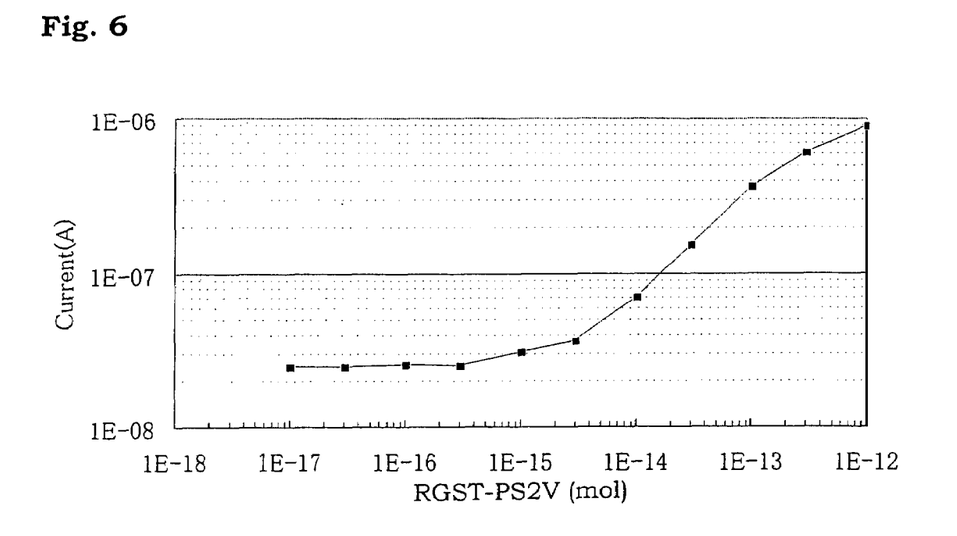
Figure 7:
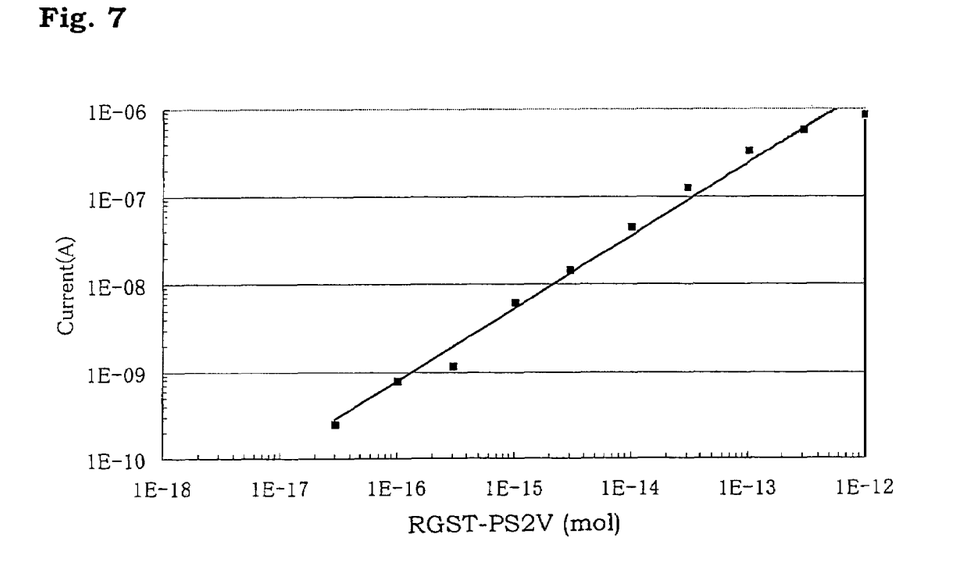

From the results of FIGS. 6 and 7, the dependency upon the amount of rGST-PS2V was confirmed within the range of $1\times10^{-17}$ mol~$1\times10^{-12}$ mol (10 amol~1 pmol) with reproducibility (variations) of 10% or less in the measurement repeated three times. The signal level of 0 mol of rGST-PS2V was deducted as a background current value from the peak current value of each of the samples having different numbers of rGST-PS2V molecules (0 correction). The thus confirmed dependency upon rGST-PS2V showed a good linearity within the range of $1\times10^{-17}$ mol~$1\times10^{-12}$ mol (10 amol~1 pmol). This shows an amol-order detectability regarding, for example, the protein of rGST-PS2V if the electrochemical detection of ALP using the substrate pMPP is applied to Sandwich-ELISA.

Example 3

Determination of rGST-PS2V by Competitive Assay (1) Immobilization of rGST-PS2V to Solid Phase A TBS solution of 1.45 μg/mL of rGST-PS2V prepared as described above was added to a 96-well plate (Cliniplate, produced by Labsystems) by 50 μL/well and allowed to stand at room temperature for two hours. The plate was washed with TBS-T containing 0.1% w/v Block Ace by 0.32 mL/well three times. A 50 mM Tris-HCl 150 mM NaCl solution containing 25% w/v Block Ace was added by 300 μL/well and allowed to stand at 37° C. for an hour for blocking.

(2) Measurement of rGST-PS2V

Solutions of normal serum containing 0 to 31 pmol of rGST-PS2V were added to the plate prepared as described above by 25 μL/well. Subsequently, a 0.03 μg/mL solution of the rabbit anti-SSMAG antibody prepared as described above (an antibody which specifically recognizes PS2V) was added by 25 μL/well and allowed to react at 37° C. for an hour. After reaction, the plate was washed with TBS-T containing 0.1% w/v Block Ace by 0.32 mL/well three times. Thereafter, a TBS-T solution of a 1000-fold dilution of anti-rabbit IgG-HRP (produced by DAKO Japan Co., Ltd.) containing 0.1% w/v Block Ace was added by 50 μL/well and allowed to react at 37° C. for an hour.

Figure 8:
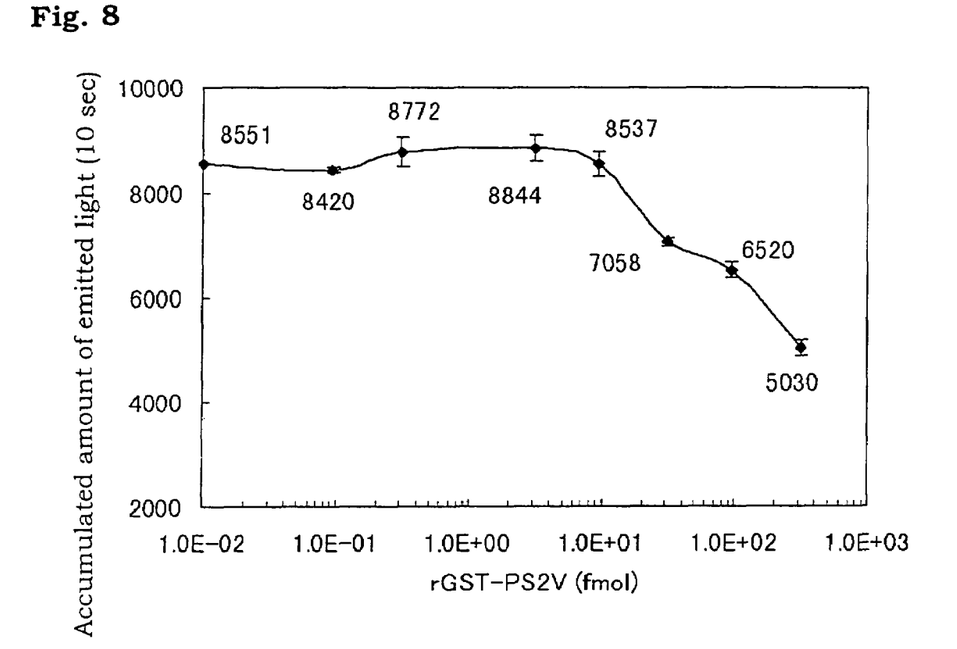

The plate was washed with TBS-T containing 0.1% w/v Block Ace by 0.32 mL/well three times. Subsequently, luminol (Super Signal ELISA Pico, produced by Pierce), which is a luminescent substrate, was added by 80 μL/well and allowed to react at 30° C. for 5 minutes. When five minutes elapsed from the beginning of enzymatic reaction, the accumulated amount of light emitted for 10 seconds was measured using Labsystems Luminoskan. FIG. 8 shows the results. It was confirmed that the competitive assay was also able to measure rGST-PS2V.

Example 4

Detection of rGST-PS2V by Competitive Assay (1) Fixation of rGST-PS2V to Solid Phase A TBS solution of 1.45 μg/mL of rGST-PS2V prepared as described above was fed onto a 96-hole plate (Cliniplate, produced by Labsystems) by 50 μL/well and allowed to stand at room temperature for an hour. The plate was washed with TBS-T containing 0.1% w/v Block Ace by 300 μL/well three times. A 50 mM Tris-HCl 150 mM NaCl solution containing 25% w/v Block Ace was added by 305 μL/well and allowed to stand at 37° C. for an hour for blocking.

(2) Detection of rGST-PS2V by Electrochemical Detection

On the plate prepared as described above, normal serum solutions containing 0 to 1 mol of rGST-PS2V were fed by 25 μL/well. Subsequently, 0.1 mg/ml of the rabbit anti-SSMAG antibody (the primary antibody) prepared as described above was added by 25 μL/well and allowed to react at 37° C. for an hour. The plate was washed with TBS-T containing 0.1% w/v of Block Ace by 300 μL/well three times. Thereafter, 50 μL of a TBS-T solution (containing 0.1% w/v of Block Ace) containing a 4,000-fold dilution of anti-rabbit IgG-ALP (the secondary antibody (produced by DAKO) were added and allowed to react at 37° C. for an hour.

Figure 9:
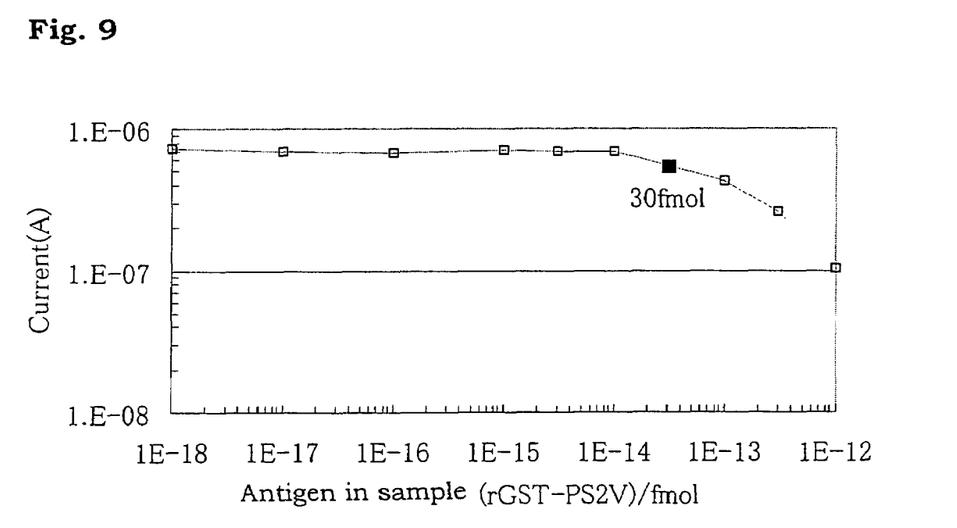

FIG. 9 shows the results of measurement. Change was recognized when the amount of the antigen rGST-PS2V in the sample exceeds 30 fmol, and it is considered that the competitive assay can be established with a detection sensitivity of 30 fmol.

INDUSTRIAL APPLICABILITY

According to the present invention, since PS2V can be detected with high sensitivity using body fluid samples, there can be provided test data useful for early diagnosis of sporadic Alzheimer's disease.

The invention claimed is:

1. A method of detecting a presenilin-2 variant that has a deletion of the amino acid sequence encoded by exon 5 (PS2V), said method comprising:

(a) reacting a test sample with a primary antibody, so as to form a complex between said primary antibody and any PS2V present in said test sample, wherein the primary antibody is immobilized on a solid phase and specifically recognizes a region including the amino acid sequence of Ser-Ser-Met-Ala-Gly (SEQ ID NO:7) at the C terminal of the amino acid sequence of SEQ ID NO:2;

(b-1) reacting the complex with a secondary antibody which is marked with a label and specifically recognizes the amino acid sequence consisting of Glu-Asn-Thr-Ala-Gln-Trp-Arg-Ser-Gln-Glu-Asn-Glu-Glu-Asp-Gly-Glu-Glu (SEQ ID NO: 9), or (b-2) reacting the complex with a secondary antibody which is biotinylated and subsequently reacting the secondary antibody reacted complex with an avidinated or streptoavidinated label, wherein the secondary antibody specifically recognizes the amino acid sequence consisting of Glu-Asn-Thr-Ala-Gln-Trp-Arg-Ser-Gln-Glu-Asn-Glu-Glu-Asp-Gly-Glu-Glu (SEQ ID NO: 9), or (b-3) reacting the complex with a secondary antibody which is biotinylated, subsequently reacting the secondary antibody reacted complex with avidin or streptoavidin and subsequently reacting the avidin or streptoavidin reacted complex with a biotinylated label, wherein the secondary antibody specifically recognizes the amino acid sequence consisting of Glu-Asn-Thr-Ala-Gln-Trp-Arg-Ser-Gln-Glu-Asn-Glu-Glu-Asp-Gly-Glu-Glu (SEQ ID NO: 9), or (b-4) reacting the complex with a secondary antibody and subsequently reacting the secondary antibody reacted complex with an antibody which is marked with a label and which specifically recognizes said secondary antibody, wherein the secondary antibody specifically recognizes the amino acid sequence consisting of Glu-Asn-Thr-Ala-Gln-Trp-Arg-Ser-Gln-Glu-Asn-Glu-Glu-Asp-Gly-Glu-Glu (SEQ ID NO: 9); and (c) detecting the amount of label captured by the complex so as to detect said PS2V in the test sample wherein PS2V is encoded by a cDNA sequence represented by SEQ ID NO: 4 and PS2 is encoded by a cDNA sequence represented by SEQ ID NO: 3.

2. The method of claim 1, wherein the label in step (b-1) or (b-4) is a radio isotope, fluorescent molecule, luminous molecule, chromophore, or ferrocene.

3. A method of detecting a presenilin-2 variant that has a deletion of the amino acid sequence encoded by exon 5 (PS2V), said method comprising:

(a) reacting a test sample with a primary antibody, so as to form a complex between said primary antibody and any PS2V present in said test sample, wherein the primary antibody is immobilized on a solid phase and specifically recognizes the amino acid sequence consisting of Glu-Asn-Thr-Ala-Gln-Trp-Arg-Ser-Gln-Glu-Asn-Glu-Glu-Asp-Gly-Glu-Glu (SEQ ID NO: 9);

(b-1) reacting the complex with a secondary antibody which is marked with a label and specifically recognizes a region consisting of the amino acid sequence Ser-Ser-Met-Ala-Gly (SEQ ID NO:7) at the C terminal of the amino acid sequence of SEQ ID NO:2, or (b-2) reacting the complex with a secondary antibody which is biotinylated and subsequently reacting the secondary antibody reacted complex with an avidinated or streptoavidinated label, wherein the secondary antibody specifically recognizes a region consisting of the amino acid sequence Ser-Ser-Met-Ala-Gly (SEQ ID NO:7) at the C terminal of the amino acid sequence of SEQ ID NO:2, or (b-3) reacting the complex with a secondary antibody which is biotinylated, subsequently reacting the secondary antibody reacted complex with avidin or streptoavidin and subsequently reacting the avidin or streptoavidin reacted complex with a biotinylated label, wherein the secondary antibody specifically recognizes a region consisting of the amino acid sequence Ser-Ser-Met-Ala-Gly (SEQ ID NO:7) at the C-terminal of the amino acid sequence of SEQ ID NO:2, or (b-4) reacting the complex with a secondary antibody and subsequently reacting the secondary antibody reacted complex with an antibody which is marked with a label and which specifically recognizes said secondary antibody, wherein the secondary antibody specifically recognizes PS2V a region consisting of the amino acid sequence Ser-Ser-Met-Ala-Gly (SEQ ID NO:7) at the C-terminal of the amino acid sequence of SEQ ID NO:2; and (c) detecting the amount of label captured by the complex so as to detect said PS2V in the test sample wherein PS2V is encoded by a cDNA sequence represented by SEQ ID NO: 4 and PS2 is encoded by a cDNA sequence represented by SEQ ID NO: 3.

4. A method of detecting a presenilin-2 variant that has a deletion of the amino acid sequence encoded by exon 5 (PS2V), said method comprising:

(a) reacting a test sample with a primary antibody, so as to form a complex between said primary antibody and any PS2V present in said test sample, wherein the primary antibody is immobilized on a solid phase and specifically recognizes PS2V a region including the amino acid sequence of Ser-Ser-Met-Ala-Gly (SEQ ID NO:7) at the C-terminal of the amino acid sequence of SEQ ID NO:2;

(b-1) reacting the complex with a secondary antibody which labeled with a first enzyme and specifically recognizes the amino acid sequence consisting of Glu-Asn-Thr-Ala-Gln-Trp-Arg-Ser-Gln-Glu-Asn-Glu-Glu-Asp-Gly-Glu-Glu (SEQ ID NO: 9), or (b-2) reacting the complex with a secondary antibody which is biotinylated and subsequently reacting the secondary antibody reacted complex with an avidinated or streptoavidinated enzyme as a second enzyme, wherein the secondary antibody specifically recognizes the amino acid sequence consisting of SEQ ID NO: 9, or (b-3) reacting the complex with a secondary antibody which is biotinylated and subsequently reacting the secondary antibody reacted complex with avidin or streptoavidin and subsequently reacting the avidin or streptoavidin reacted complex with a biotinylated enzyme as a third enzyme, wherein the secondary antibody specifically recognizes the amino acid sequence consisting of Glu-Asn-Thr-Ala-Gln-Trp-Arg-Ser-Gln-Glu Asn-Glu-Glu-Asp-Gly-Glu-Glu (SEQ ID NO: 9), or (b-4) reacting the complex with a secondary antibody and subsequently reacting the secondary antibody reacted complex with an antibody which is labeled with a fourth enzyme and specifically recognizes said secondary antibody, wherein the secondary antibody specifically recognizes the amino acid sequence consisting of Glu-Asn-Thr-Ala-Gln-Trp-Ar-Ser Gln-Glu-Asn-Glu-Glu-Asp-Gly-Glu-Glu (SEQ ID NO: 9); and (c-1) adding a first substrate for the first enzyme and detecting a product generated by enzymatic reaction of the first enzyme and the first substrate, or (c-2) adding a second substrate for the second enzyme and detecting a product generated by enzymatic reaction of the second enzyme and the second substrate, or (c-3) adding a third substrate for the third enzyme and detecting a product generated by enzymatic reaction of the third enzyme and third substrate, or (c-4) adding a fourth substrate for the fourth enzyme and detecting a product generated by enzymatic reaction of the fourth enzyme and the fourth substrate wherein PS2V is encoded by a cDNA sequence represented by SEQ ID NO: 4 and PS2 is encoded by a cDNA sequence represented by SEQ ID NO: 3.

5. The method of claim 4, wherein first enzyme, second enzyme, third enzyme or fourth enzyme are each independently selected from the group consisting of horseradish peroxidase, alkaline phosphatase, β-D-galactosidase, glucose-6-phosphate dehydrogenase and luciferase.

6. The method of claim 5, wherein the first enzyme, second enzyme, third enzyme or fourth enzyme are each alkaline phosphatase, and the first substrate, second substrate, third substrate or fourth substrate are each a phosphate of a phenol derivative having an electron donative group at o-position and p-position.

7. The method of claim 6, wherein the electron donative group is a lower alkoxy group.

8. A method of detecting a presenilin-2 variant that has a deletion of the amino acid sequence encoded by exon 5 (PS2V), said method comprising
(a) reacting a test sample with a primary antibody, so as to form a complex between said primary antibody and any PS2V present in said test sample, wherein the primary antibody is immobilized on a solid phase and specifically recognizes the amino acid sequence consisting of Glu-Asn-Thr-Ala-Gln-Trp-Arg-Ser-Gln-Glu-Asn-Glu-Glu-Asp-Gly-Glu-Glu (SEQ ID NO: 9);
(b-1) reacting the complex with a secondary antibody which is labeled with a first enzyme and specifically recognizes region consisting of the amino acid sequence ef Ser-Ser-Met-Ala-Gly (SEQ ID NO:7) at the C-terminal of the amino acid sequence of SEQ ID NO:2, or
(b-2) reacting the complex with a secondary antibody which is biotinylated and subsequently reacting the secondary antibody reacted complex with an avidinated or streptoavidinated enzyme as a second enzyme, wherein the secondary antibody specifically recognizes a region consisting of the amino acid sequence ef Ser-Ser-Met-Ala-Gly (SEQ ID NO:7) at the C-terminal of the amino acid sequence of SEQ ID NO:2, or
(b-3) reacting the complex with a secondary antibody which is biotinylated, subsequently reacting the complex with avidin or streptoavidin and subsequently reacting the avidin or streptoavidin reacted complex with a biotinylated enzyme as a third enzyme, wherein the secondary antibody specifically recognizes a region consisting of the amino acid sequence Ser-Ser-Met-Ala-Gly (SEQ ID NO:7) at the C-terminal of the amino acid sequence of SEQ ID NO:2, or
(b-4) reacting the complex with a secondary antibody and subsequently reacting the secondary antibody complex with an antibody which is labeled with a fourth enzyme and specifically recognizes said secondary antibody, wherein the secondary antibody specifically recognizes a region consisting of the amino acid sequence Ser-Ser-Met-Ala-Gly (SEQ ID NO:7) at the C-terminal of the amino acid sequence of SEQ ID NO: 2; and
(c-1) adding a first substrate for the first enzyme and detecting a product generated b enzymatic reaction of the first enzyme and the first substrate, or
(c-2) adding a second substrate for the second enzyme and detecting a product generated by enzymatic reaction of the second enzyme and the second substrate, or
(c-3) adding a third enzyme for the third enzyme and detecting a product generated by enzymatic reaction of the third enzyme and the third substrate, or
(c-4) adding a fourth substrate for the fourth enzyme and detecting a product generated by enzymatic reaction of the fourth enzyme and fourth substrate
wherein PS2V is encoded by a cDNA sequence represented by SEQ ID NO: 4 and PS2 is a polypeptide encoded by a cDNA sequence represented by SEQ ID NO: 3.

* * * * *